(12) United States Patent
Kuo et al.

(10) Patent No.: US 8,709,438 B2
(45) Date of Patent: Apr. 29, 2014

(54) **VACCINE COMPOSITION AGAINST *STREPTOCOCCUS PYOGENES***

(75) Inventors: Chih-Feng Kuo, Kaohsiung (TW); Nina Tsao, Kaohsiung (TW)

(73) Assignee: I-Shou University, Kaohsiung (TW)

( * ) Notice: Subject to any disclaimer, the term of this patent is extended or adjusted under 35 U.S.C. 154(b) by 0 days.

(21) Appl. No.: 13/546,637

(22) Filed: Jul. 11, 2012

(65) Prior Publication Data

US 2013/0315946 A1 Nov. 28, 2013

(30) Foreign Application Priority Data

May 23, 2012 (TW) .............................. 101118374 A (51) Int. Cl.
*A61K 39/09* (2006.01)

(52) U.S. Cl.
CPC .................................. *A61K 39/092* (2013.01)
USPC .................................... 424/190.1; 424/244.1

(58) Field of Classification Search
CPC .................................................. A61K 39/092
See application file for complete search history.

(56) References Cited

U.S. PATENT DOCUMENTS 7,132,107 B2 11/2006 Adamou et al.
7,504,110 B2 3/2009 Mizrachi Nebenzahl

OTHER PUBLICATIONS

Ulrich (Journal of Immune Based Therapies and Vaccines, 6:1-8, 2008).*
Harlow et al (Antibodies a Laboratory Manual; Cold Spring Harbor Laboratory, 1988, chapter 5, pp. 53-137).*
Nina Tsao et al., Immunization with synthetic peptides derived from the C-terminal regions of streptococcal pyrogenic exotoxin B protects mice against lethal challenge of group A *Streptococcus*, Conference Manual of Taiwan Society of Microbiology, Dec. 18, 2011, pp. 67-68.
Y-H Luo et al., Streptococcal pyrogenic exotoxin B antibodies in a mouse model of glomerulonephritis, Kidney International, Jul. 18, 2007, pp. 716-724, vol. 72.

* cited by examiner

*Primary Examiner* — Patricia A Duffy
(74) *Attorney, Agent, or Firm* — Muncy, Geissler, Olds & Lowe, P.C.

(57) ABSTRACT

The present invention relates to a vaccine composition against *Streptococcus pyogenes* infection comprising an amino acid sequence having C-terminal fragment of streptococcal pyrogenic exotoxin B, and a pharmaceutical acceptable adjuvant.

8 Claims, 7 Drawing Sheets

VACCINE COMPOSITION AGAINST *STREPTOCOCCUS PYOGENES*

BACKGROUND OF THE INVENTION

1. Field of the Invention

The present invention generally relates to a vaccine composition and, more particularly to a vaccine composition against *Streptococcus pyogenes* infection and comprising amino acid sequence of streptococcal pyrogenic exotoxin B.

2. Description of the Related Art

*Streptococcus pyogenes* is one of major causes of human disease and suffering worldwide, generally leading to invasive infection on organisms. *S. pyogenes* has several virulence factors that enable it to attach to hosts and to evade the immune response thereof. Wherein, streptococcal pyrogenic exotoxin B (SPE B) is one of major virulence factors, and which can degrade properdin and complements, especially for complement C3 in hosts, blocking downstream response of complement system, such as anti-microbial function of neutrophils, so as to result in serious invasion of *S. pyogenes*, tissue damages, even death.

The SPE B is a conserved gene of *S. pyogenes*, with almost all strains of *S. pyogenes* comprising speB gene, and with 89 speB alleles being found worldwide. The SPE B has 398 amino acids, being around 42 KDa, including a prosegment (about 14 KDa) at N-terminal thereof, and a protease (mSPE B) being 28 KDa.

A conventional vaccine against *Streptococcus pyogenes* infection, comprising an inactivated SPE B (being an immunogenic virulence protein) that is prepared by mutating the $192^{nd}$ amino acid (cysteine) of SPE B to serine via site direct mutagenesis, is currently developed, with the conventional vaccine activating response of complement and downstream mechanism thereof to achieve anti-microbes effects in hosts. However, 70% hosts suffer from autoimmune responses, rheumatic heart disease and nephritis for example, after inoculation of the said conventional vaccine, and therefore, it is insufficient in practice use and poor to be further applied on clinical medicine.

Hence there is a need of providing a new vaccine, for improving the said disadvantages.

SUMMARY OF THE INVENTION

The primary objective of this invention is to provide a vaccine composition against *S. pyogenes* infection, which can induce immune responses in hosts generate antibody specifically against streptococcal pyrogenic exotoxin B (SPE B).

The secondary objective of this invention is to provide a vaccine composition against *S. pyogenes* infection, which will not cause to serious autoimmune responses, such as rheumatic heart disease and nephritis.

A vaccine composition against *Streptococcus pyogenes* infection comprises an amino acid sequence comprising C-terminal fragments of streptococcal pyrogenic exotoxin B, and a pharmaceutical acceptable adjuvant.

The vaccine composition according to the present invention comprises the said amino acid sequence that is selected from a group of SEQ ID NO. 2, 6, 8, and 9, preferably being SEQ ID NO. 6 and 8.

The vaccine composition according to the present invention comprises the said amino acid sequence and the pharmaceutical acceptable adjuvant in a ratio of 1 μg: 1 μl, wherein the pharmaceutical acceptable adjuvant is complete Freund's adjuvant or incomplete Freund's adjuvant, and the said amino acid sequence comprising C-terminal fragments of SPE B according to *Streptococcus pyogenes* M49 or *Streptococcus pyogenes* emm 1.

The vaccine composition according to the present invention is characterized in that the said amino acid sequence is coupled to a pharmaceutically acceptable carrier, preferably keyhole limpet haemocyanine (KLH).

Further scope of the applicability of the present invention will become apparent from the detailed description given hereinafter. However, it should be understood that the detailed description and specific examples, while indicating preferable embodiments of the invention, are given by way of illustration only, since various more will become apparent to those skilled in the art from this detailed description.

BRIEF DESCRIPTION OF THE DRAWINGS

The present invention will become more fully understood from the detailed description given herein below and the accompanying drawings which are given by way of illustration only, and thus are not limitative of the present invention, and wherein:

FIG. 1 is a bar chart illustrating ELISA data of amino acid sequences A1 to A3 under $OD_{650}$;

FIG. 2 is a bar chart illustrating related binding ability between compliment C3 and amino acid sequences A2-0, A2-1, A2-2, A2-3, A2-4, A2-5, and A2-6;

FIG. 3 is a chart illustrating the titer of immune responses in mice of groups B1-B3;

FIG. 4 is a chart illustrating skin lesions of mice in groups B1-B3;

FIG. 5 is a line chart illustrating survival rates of mice in groups B1 to B3;

FIG. 6(*a*)~(*f*) are photos illustrating skin lesions of mice in groups B1-1, B1-2, 2-1 and 2-2;

FIG. 7 is a line chart illustrating survival rates of mice in groups B1-1, B1-2, B2-1 and B2-2;

FIG. 8 is a line chart illustrating survival rates of mice in groups B3-1, B3-2, B4-1 and B4-2;

FIG. 9(*a*)~(*b*) are photos illustrating histological section of mice's kidney in groups B1-1 and B1-2.

All figures are drawn for ease of explaining the basic teachings of the present invention only; the extensions of the figures with respect to number, position, relationship, and dimensions of the parts to form the preferred embodiment will be explained or will be within the skill of the art after the following teachings of the present invention have been read and understood. Further, the exact dimensions and dimensional proportions conforming to specific force, weight, strength, and similar requirements will likewise be within the skill of the art after the following teachings of the present invention have been read and understood.

DETAILED DESCRIPTION OF THE INVENTION

The present invention relates to a vaccine composition against *S. pyogenes* infection, comprising an amino acid sequence comprising C-terminal fragment of streptococcal pyrogenic exotoxin B (SPE B) and a pharmaceutical acceptable adjuvant. More specifically, the C-terminal sequences of SPE B is an activated fragment that binds to complement, and which can induce immune response in hosts to generate antibodies specifically against SPE B, without leading to serious autoimmune responses. The antibodies will specifically bind to the activated fragment of SPE B, interfering with the binding between SPE B and complement, so that, the immune response of the complement in hosts can be successfully conducted when suffers from *S. pyogenes* infection but be block by SPE B. Furthermore, since inactivated fragment of SPE B has been deleted, the vaccine composition can reduce the side effects of autoimmune responses caused by SPE B.

With reference to TABLE 1, in a preferable embodiment of the present invention, the vaccine composition comprises the C-terminal fragments of SPE B being GISVDMDYGPSSG-SAGSSRVQRALKENFGYNQSVHQINRGDFSKQ DWEAQIDKELSQNQPVYYQGVGKVG-GHAFVIDGADGRNFYHVN WGWGGVSDGFFRLDAL-NPSALGTGGGAGGFNGYQSAVVGIKP (as set forth in SEQ ID NO: 2), GADGRNFYHVNWGWG (as set forth in SEQ ID NO: 6), ALGTGGGAGGFNGYQSAVVGIKP (as set forth in SEQ ID NO: 8), GADGRNFYHVNWGWG-GVSDGFFRLDALNPSALGTGGGAGGFNG YQSAV-VGIKP (as set forth in SEQ ID NO: 9) and a combination thereof. More preferably, the vaccine composition comprises the C-terminal fragment as set forth in SEQ ID NO: 6 or 8, being significantly effective in inducing hosts' immune response to generate antibodies specifically against SPE B.

TABLE 1 the amino acid sequence in a preferable embodiment of the present invention

| NO. | Sequence |
| --- | --- |
| SEQ ID NO: 1 | Sequence of SEP B |
| SEQ ID NO: 2 | SPE $B_{269-398}$ |
| SEQ ID NO: 6 | SPE $B_{346-360}$ |
| SEQ ID NO: 8 | SPE $B_{376-398}$ |
| SEQ ID NO: 9 | SPE $B_{345-398}$ |

Preferably, the pharmaceutical acceptable adjuvant of the vaccine composition of the preferable embodiment can be selected form complete Freund's adjuvant (CFA) or incomplete Freund's adjuvant (IFA). Furthermore, a ratio between the amino acid sequence and pharmaceutical acceptable adjuvant in the preferable embodiment of vaccine composition is 1 µg:1 µl. As an example, a vaccine composition of a preferable example in the present invention comprises 50 µg the amino acid sequence and 50 µl the pharmaceutical acceptable adjuvant mixed with each other, with the vaccine composition being effective in inducing immune response in hosts to generate antibodies against SPE B.

Also, the said amino acid sequence in the vaccine composition in the preferable embodiment of the present comprises the C-terminal fragment of SPE B according to *Streptococcus pyogenes* M49 or *Streptococcus pyogenes* emm 1, so as to induce immune response in hosts to generate antibodies specifically against SPE B of *Streptococcus pyogenes* M49 or *Streptococcus pyogenes* emm 1. In this way, skin ulceration, as well as high mortality, caused by *Streptococcus pyogenes* M49 or *Streptococcus pyogenes* emm 1 infection can be effectively relieved.

In the following paragraphs, the binding between the said amino acid sequence and complement C3, and the antigenicity of the said amino acid sequence are determined in trial (A) to (C), for confirming the benefits of the vaccine composition of the present invention.

Trial (A): Binding Ability to Complement C3

With reference to TABLE 2, various amino acid sequences (including A1, A2, and A3) comprising different sequences according to SPE B are prepared, wherein the amino acid sequence A1 comprises whole fragment of SPE B, with the $192^{nd}$ amino acid (cysteine) being mutated to serine, the amino acid sequence A2 comprises $1^{st}$ to $268^{th}$ amino acids of SPE B (as set forth in SEQ ID NO: 2), and the amino acid sequence A3 comprises $296^{th}$ to $398^{th}$ amino acids of SPE B.

In the present trial, three oligonucleotides encoded the amino acid sequences A1, A2 and A3 respectively are prepared and constructed into an expressed vector individually, followed by deliberating the constructed three oligonucleotides into *E. coli* respectively (via transformation), with *E. coli* system expressing the three amino acid sequences (including A1, A2 and A3) and purifying them respectively via fast protein liquid chromatography (FPLC). In the present trial, the expressed vector is but not limit to pET24a expression vector.

Then, 0.2 µg of each amino acid sequences (including A1, A2 and A3) are coated on a 96-well ELISA plate, and sequentially reacted with a serum sample (dilution with GVB/MgEGTA), an antibody against complement C3, a HRP linked second antibody and TMB (for coloration), and absorbance of each well are tested under $OD_{650}$ to identifying the binding ability of each amino acid sequence (including A1, A2 and A3) to complement C3.

TABLE 2

Various Amino acid sequences in Trial (A)

| NO. | Sequences |
| --- | --- |
| A1 | inactivated SPE B (comprising C192S mutation) |
| A2 | SPE $B_{1-268}$ |
| A3 | SPE $B_{269-398}$ (as set forth in SEQ ID NO: 2) |

Figure 1:
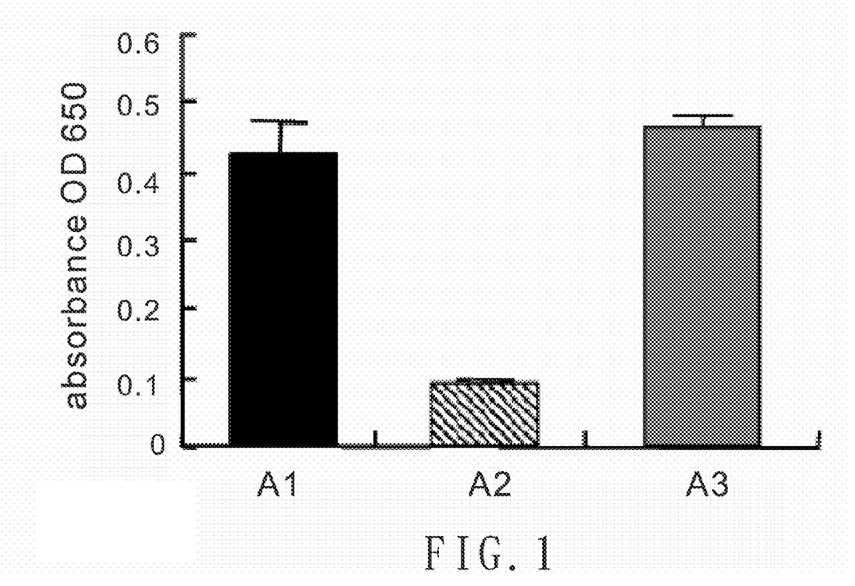

In FIG. 1, it is proved that, the amino acid sequence comprising SPE $B_{269-398}$ (as set forth in SEQ ID NO: 2) is an activated fragment that binds to complement C3, and thus that is capable of being used as an immunogenic virulence protein in vaccine composition, for inducing hosts immune response to generate antibody.

With reference to TABLE 3, another six amino acid sequences (including A2-0, A2-1, A2-2, A2-3, A2-4, A2-5 and A2-6) are also prepared and demonstrated, wherein the six amino acid sequences can be artificially synthesized, or expressed via *E. coli* system by constructing 6 oligonucleotides encoded six amino acid sequences (including A2-0, A2-1, A2-2, A2-3, A2-4, A2-5 and A2-6) into an expressed vector (the expressed vector is but not limit to pET42a expression vector) individually, with the six oligonucleotides being inserted at a site after a nucleotide sequence encoded GST tag protein, and then deliberating the constructed six oligonucleotides into *E. coli* respectively (via transformation), with the *E. coli* system expressing the six amino acid sequences (including A2-0, A2-1, A2-2, A2-3, A2-4, A2-5 and A2-6) and purifying them respectively via the fast protein liquid chromatography (FPLC). Preferably, the six amino acid sequences are artificially synthesized in the present trial. Next, the binding ability of each amino acid sequence to compliment C3 is also determined via ELISA according to the process described above.

TABLE 3

Various Amino acid sequences in Trial (A)

| NO. | Sequences |
| --- | --- |
| A2-0 | SPE B (comprising C192S mutation) |
| A2-1 | SPE $B_{301-315}$ (as set forth in SEQ ID NO: 3) |
| A2-2 | SPE $B_{316-330}$ (as set forth in SEQ ID NO: 4) |
| A2-3 | SPE $B_{331-345}$ (as set forth in SEQ ID NO: 5) |
| A2-4 | SPE $B_{346-360}$ (as set forth in SEQ ID NO: 6) |

TABLE 3-continued

Various Amino acid sequences in Trial (A)

| NO. | Sequences |
|---|---|
| A2-5 | SPE $B_{356-375}$ (as set forth in SEQ ID NO: 7) |
| A2-6 | SPE $B_{376-398}$ (as set forth in SEQ ID NO: 8) |

Figure 2:
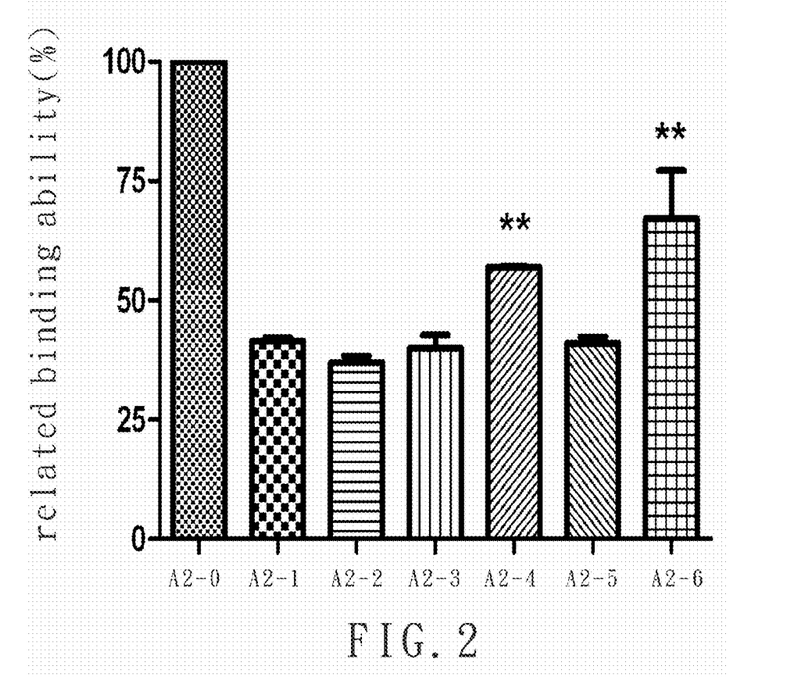
Figure 3:
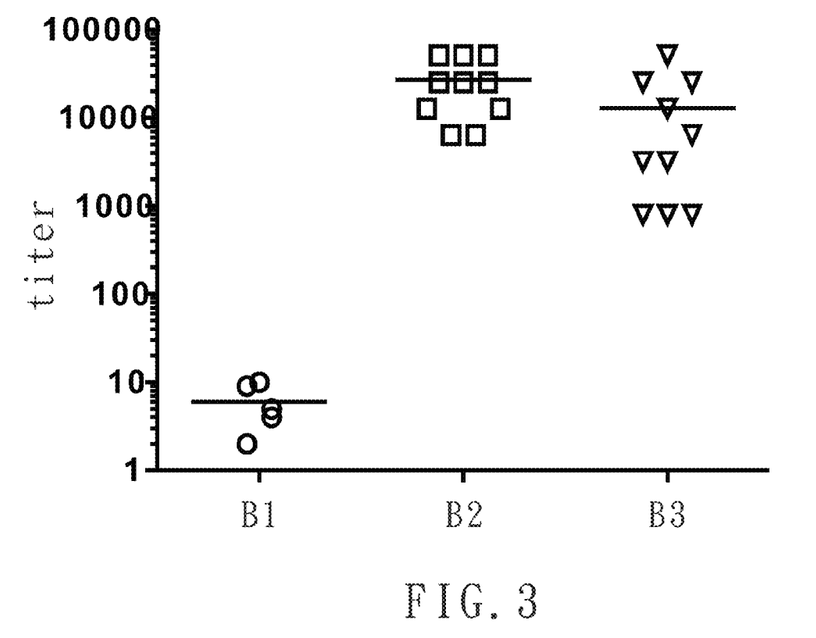
Figure 4:
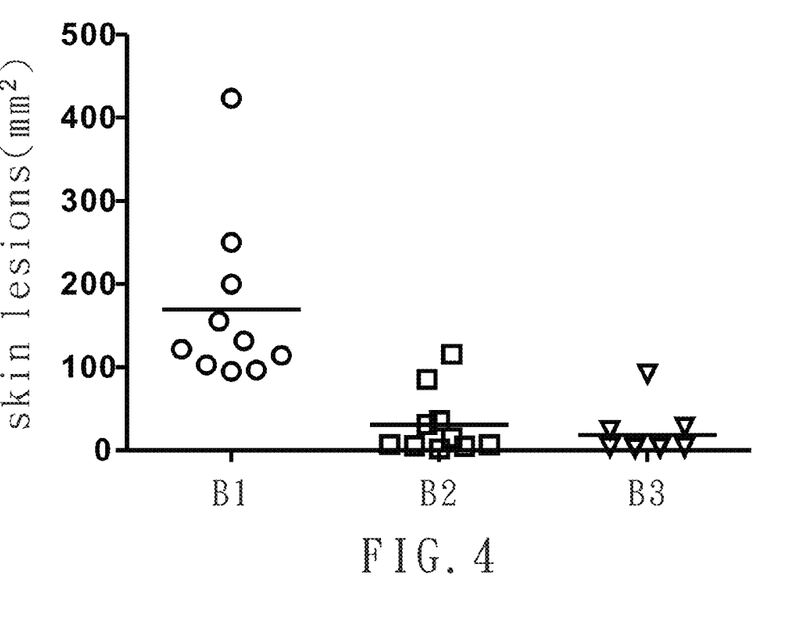
Figure 5:
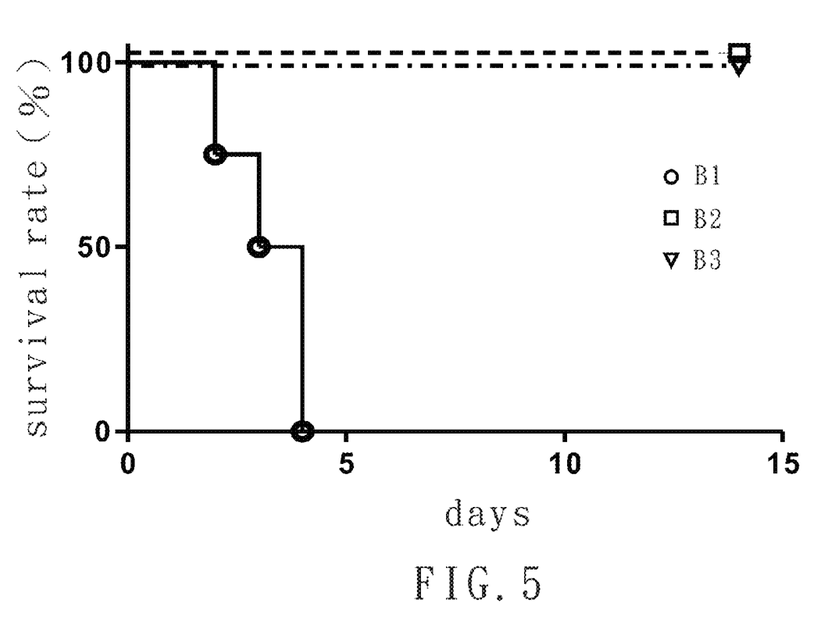
Figure 6:
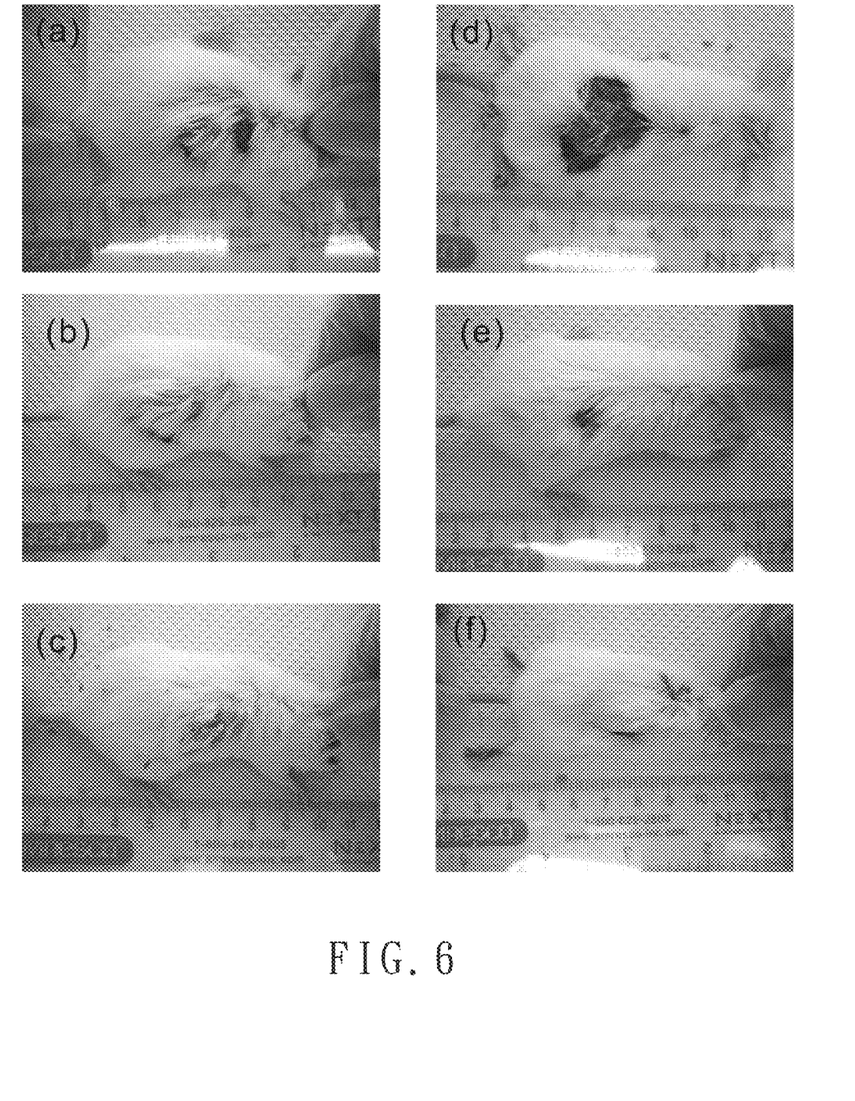
Figure 7:
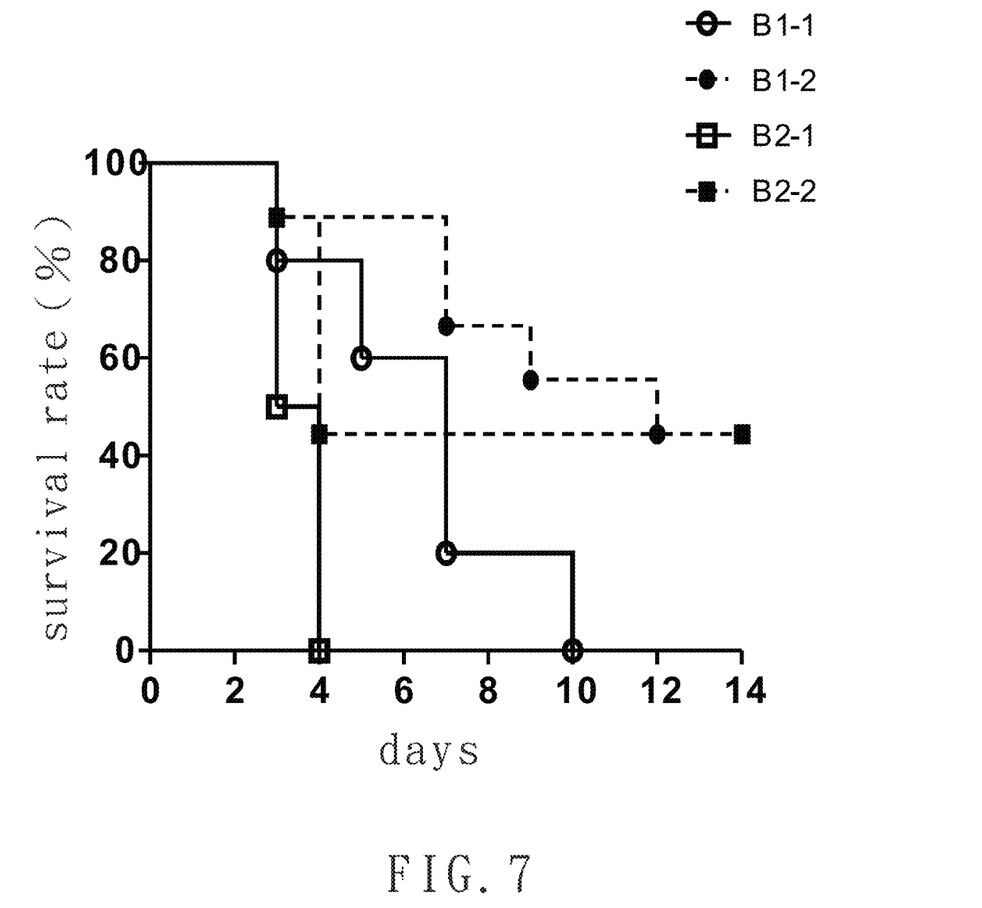
Figure 8:
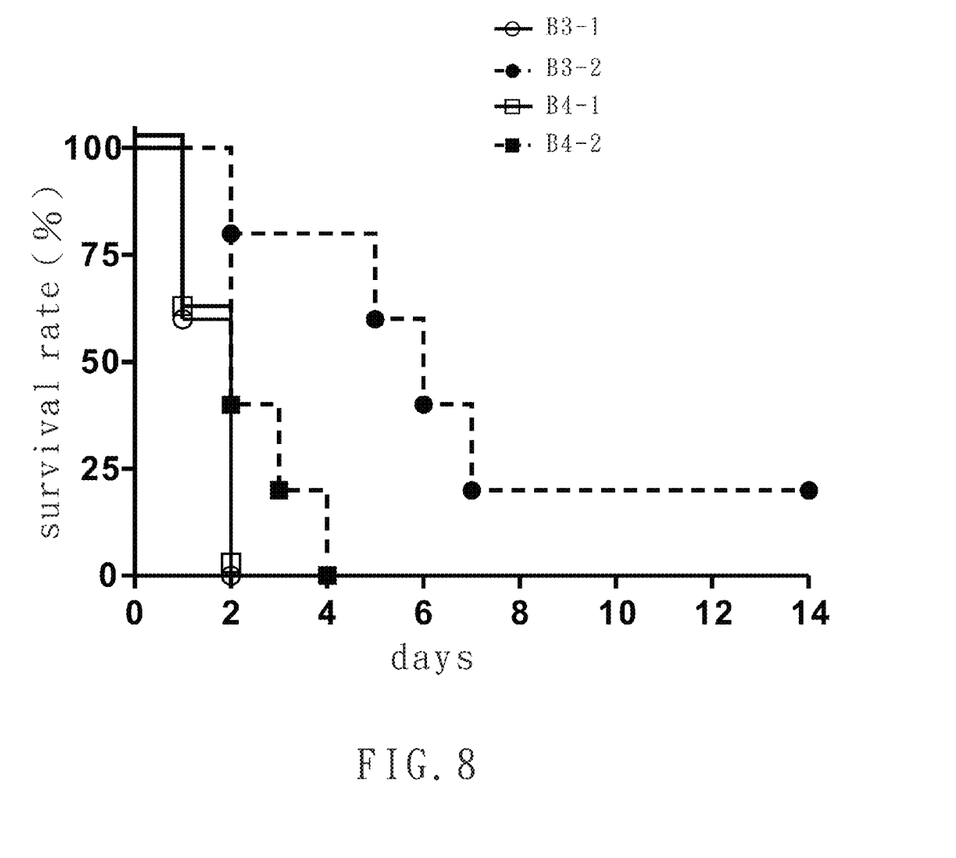

As shown in FIG. 2, the binding ability of amino acid sequences A2-4 and A2-6 to the complement C3 is significantly higher (with around more than 50%) than that of other amino acid sequences in comparison with a reference of A2-0. It is noted that the amino acid sequence comprising C-terminal fragment of SPE B, especially for the $346^{th}$ to $360^{th}$, and the $376^{th}$ to $398^{th}$ amino acids of SPE B, is an activated fragment that binds to complement C3.

Trial (B): Animal Infection

Figure 9:
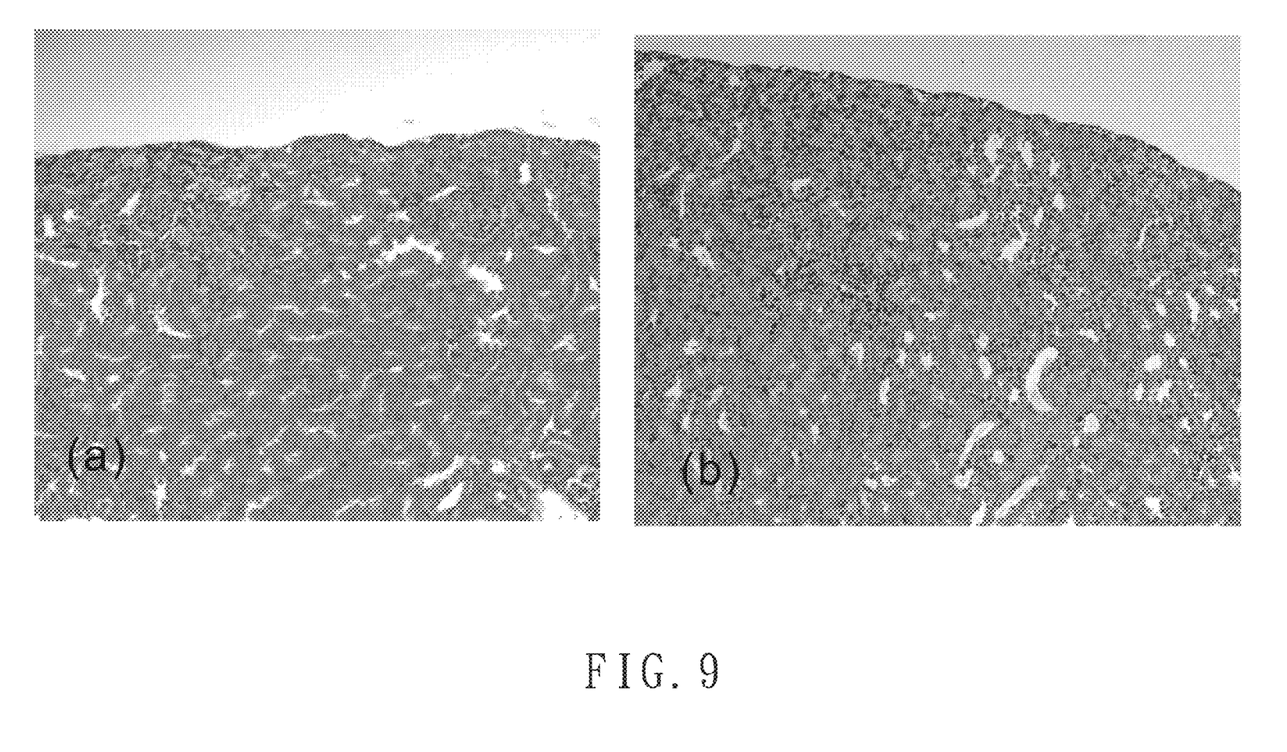

For proving the amino acid sequence comprising C-terminal fragment of SPE B, especially comprising SPE $B_{346-360}$ (set forth in SEQ ID NO: 6) or SPE $B_{376-398}$ (set forth in SEQ ID NO: 8), being capable of inducing immune response in hosts to generate antibody against SPE B, and further relieving symptoms of *S. pyogenes* infection, a vaccination is carried out on mice by inoculating various vaccine compositions that comprise the amino acid sequence as set forth in SEQ ID NO: 6 or 8 respectively, and then tissue lesions and mortality of the mice are monitored and recorded after vaccination.

With reference to TABLE 4, 30 BALB/c mice purchased from National Applied Research Laboratories in Taiwan are randomly assigned to three groups, including B1, B2 and B3, with mice in B1 being untreated, and with mice in B2 and B3 being treated with the vaccine compositions comprising the amino acid sequences set forth in SEQ ID NO: 6 and 8 respectively.

In the present trial, the amino acid sequences set forth in SEQ ID NO: 6 and 8 are coupled to keyhole limpet haemocyanine (KLH) respectively for promoting the immunogenicity thereof, and then the amino acid sequences set forth in SEQ ID NO: 6 and 8 are further mixed with CFA or IFA before following immunization.

TABLE 4

| Groups Assignment in the Trial (B) | |
|---|---|
| Groups | Inoculations |
| B1 (Control) | untreated |
| B2 | SPE $B_{346\sim360}$ (as set forth in SEQ ID NO: 6) + KLH |
| B3 | SPE $B_{376\sim398}$ (as set forth in SEQ ID NO: 8) + KLH |

In the present trial, the mice in groups B1 to B3 are intraperitoneally immunized for three times, by inoculating 50 μg the amino acid sequence set forth in SEQ ID NO: 6 (or SEQ ID NO: 8) and CFA for the first time, and then carrying out additional two injections every two weeks with 25 μg the amino acid sequence set forth in SEQ ID NO: 6 (or SEQ ID NO: 8) and IFA. Next, titers of each group are tested and confirmed if the titer of group B2 reaches to 10000 (as shown in FIG. 3). After that, a strain of *Streptococcus pyogenes* M49 (ZN131) obtained from Prof. Jiunn-Jong Wu of National Cheng Kung University in TAIWAN is prepared and inoculated to mice's back in a dosage of $2\times10^8$~$3\times10^8$ CFU/mouse after vaccination, and skin lesions and mortality of mice in each groups are recorded in the $3^{rd}$ and $14^{th}$ day after inoculation individually.

In FIG. 4, it is indicated that the vaccine composition, especially for the vaccine composition comprising the amino acid sequences of SPE $B_{346\sim360}$ or SPE $B_{376\sim398}$, can effectively relieve the symptoms of *S. pyogenes* infection, such as lesions on mice back.

In FIG. 5, it is indicated that the vaccine composition, especially for the vaccine composition comprising the amino acid sequences of SPE $B_{346\sim360}$ or SPE $B_{376\sim398}$, can effectively avoid the death caused by *S. pyogenes* infection, improving survival rates of hosts that suffer from *S. pyogenes* infection.

Next, with reference to TABLE 5, another eight groups of mice are prepared, such as B1-1 (including 5 mice), B1-2 (including 9 mice), B2-1 (including 5 mice), B2-2 (including 9 mice), B3-1 (including 5 mice), and B3-2 (including 5 mice), B4-1 (including 5 mice), and B4-2 (including 5 mice), with mice in groups B1-1, B2-1, B3-1 and B4-1 being untreated, with mice in groups B1-2, B2-2, B3-2 and B4-2 being immunized with the vaccine compositions of the present invention before inoculation of a strain of *Streptococcus pyogenes* emm1 in a dosage of $1\times10^8$ CFU/mouse (being selected from strains A1 and A20, which are all obtained from Prof. Jiunn-Jong Wu of National Cheng Kung University in TAIWAN). Then, skin lesions and mortality of mice in each group are recorded in the $3^{rd}$ and $14^{th}$ day after inoculation individually.

TABLE 5

| Groups Assignment in the Trial (B) | | | |
|---|---|---|---|
| Groups | Inoculation | Strain of *Streptococcus pyogenes* emm1 | Skin Lesions |
| B1-1 | Untreated | A1 | FIG. 6(a) |
| B1-2 | KLH-SPE $B_{376\sim398}$ | A1 | FIG. 6(b)-(c) |
| B2-1 | Untreated | A20 | FIG. 6(d) |
| B2-2 | KLH-SPE $B_{376\sim398}$ | A20 | FIG. 6(e)-(f) |
| B3-1 | Untreated | A1 | FIG. 8 |
| B3-2 | KLH-SPE $B_{346\sim360}$ | A1 | FIG. 8 |
| B4-1 | Untreated | A20 | FIG. 8 |
| B4-2 | KLH-SPE $B_{346\sim360}$ | A20 | FIG. 8 |

FIGS. 6(*a*) to (*f*) show skin lesions of mice in the groups B1-1, B1-2, B2-1 and B2-2, and which indicates that skin lesions of mice in groups B1-2 and B2-2 are significantly slighter in comparison with that in groups B1-1 and B2-1. Furthermore, FIGS. 7 and 8 show that mortality of mice in groups B1-2, B2-2 (with around 40% in the $14^{th}$ day), B3-2 and B4-2 (with around 25% in the $14^{th}$ day) are higher in comparison with that in groups B1-1, B2-1, B3-1 and B4-1. It is noted that with immunization of the vaccine composition comprising an amino acid sequence having the C-terminal fragments of SPE B (especially for SPE $B_{376\sim398}$), the *S. pyogenes* infection on animal can be relieved and turned down, with slight skin lesions and a high survival rates being observed on hosts.

Trial (C): Histological Section of Kindly

In view of a paper published on kidney international journal, entitled "streptococcal pyrogenic exotoxin B antibodies in a mouse model of glomerulonephritis," (Lo. et al., 2007), mice immunized with the conventional vaccine comprising the inactivated SPE B (C192S mutation) will suffer from side effects on kidney. In the present trial, mice of groups B1-1 and 1-2 are killed to take histological section of their kidney. The histological sections of kidney of the mice are dyed via Eosin stain and analyzed by microscopy.

FIGS. 9(a) and (b) show that mice in groups B1-1 and 1-2 do not have tissue inflammation on kidney, and therefore, it is believed the vaccine composition of the present invention will not lead to autoimmune responses, nephritis for example.

Through the present invention, the vaccine composition is provided, comprising the amino acid sequence that have C-terminal fragment of SPE B, such as SPE $B_{301\sim315}$, SPE $B_{316\sim330}$, SPE $B_{331\sim345}$, SPE $B_{346\sim360}$, SPE $B_{356\sim375}$, and SPE $B_{376\sim398}$, preferably SPE $B_{346\sim360}$ and SPE $B_{376\sim398}$. With immunization of the said vaccine composition hosts, it is sufficient to induct hosts' immune response to generate antibodies against S. pyogenes, so as to avoid invasive suffering caused by S. pyogenes infection. Also, the vaccine composition of the present invention will not lead to autoimmune responses to hosts, and which reduces the incidences to nephritis and rheumatic heart.

Although the invention has been described in detail with reference to its presently preferred embodiment, it will be understood by one of ordinary skill in the art that various modifications can be made without departing from the spirit and the scope of the invention, as set forth in the appended claims.

---

What is claimed is:

1. A vaccine composition against *Streptococcus pyogenes* comprising:
   an amino acid fragment that derives from streptococcal pyrogenic exotoxin B and consists of an amino acid sequence as set forth in SEQ ID NO: 6; and a pharmaceutical acceptable adjuvant.

2. A vaccine composition against *Streptococcus pyogenes* comprising:
   an amino acid fragment that derives from streptococcal pyrogenic exotoxin B and consists of an amino acid sequence as set forth in SEQ ID NO: 8; and a pharmaceutical acceptable adjuvant.

3. The vaccine composition against *Streptococcus pyogenes* as defined in claim 1, wherein the amino acid sequence and the pharmaceutical acceptable adjuvant is mixed in a ratio of 1 µg:1 µl.

4. The vaccine composition against *Streptococcus pyogenes* as defined in claim 1, wherein the pharmaceutical acceptable adjuvant is complete Freund's adjuvant or incomplete Freund's adjuvant.

5. The vaccine composition against *Streptococcus pyogenes* as defined in claim 1, wherein the amino acid sequence is coupled to keyhole limpet haemocyanine (KLH).

6. The vaccine composition against *Streptococcus pyogenes* as defined in claim 2, wherein the amino acid sequence and the pharmaceutical acceptable adjuvant is mixed in a ratio of 1 µg:1 µl.

7. The vaccine composition against *Streptococcus pyogenes* as defined in claim 2, wherein the pharmaceutical acceptable adjuvant is complete Freund's adjuvant or incomplete Freund's adjuvant.

8. The vaccine composition against *Streptococcus pyogenes* as defined in claim 2, wherein the amino acid sequence is coupled to keyhole limpet haemocyanine (KLH).

* * * * *

SEQUENCE LISTING

<160> NUMBER OF SEQ ID NOS: 9

<210> SEQ ID NO 1
<211> LENGTH: 398
<212> TYPE: PRT
<213> ORGANISM: Streptococcus pyogenes

<400> SEQUENCE: 1

```
Met Asn Lys Lys Lys Leu Gly Val Arg Leu Leu Ser Leu Leu Ala Leu
1               5                   10                  15

Gly Gly Phe Val Leu Ala Asn Pro Val Phe Ala Asp Gln Asn Phe Ala
                20                  25                  30

Arg Asn Glu Lys Glu Ala Lys Asp Ser Ala Ile Thr Phe Ile Gln Lys
            35                  40                  45

Ser Ala Ala Ile Lys Ala Gly Ala Arg Ser Ala Glu Asp Ile Lys Leu
        50                  55                  60

Asp Lys Val Asn Leu Gly Gly Glu Leu Ser Gly Ser Asn Met Tyr Val
65                  70                  75                  80

Tyr Asn Ile Ser Thr Gly Gly Phe Val Ile Val Ser Gly Asp Lys Arg
                85                  90                  95

Ser Pro Glu Ile Leu Gly Tyr Ser Thr Ser Gly Ser Phe Asp Ala Asn
            100                 105                 110

Gly Lys Glu Asn Ile Ala Ser Phe Met Glu Ser Tyr Val Glu Gln Ile
        115                 120                 125

Lys Glu Asn Lys Lys Leu Asp Thr Thr Tyr Ala Gly Thr Ala Glu Ile
    130                 135                 140

Lys Gln Pro Val Val Lys Ser Leu Leu Asp Ser Lys Gly Ile His Tyr
145                 150                 155                 160

Asn Gln Gly Asn Pro Tyr Asn Leu Leu Thr Pro Val Ile Glu Lys Val
                165                 170                 175

Lys Pro Gly Glu Gln Ser Phe Val Gly Gln His Ala Ala Thr Gly Cys
            180                 185                 190

Val Ala Thr Ala Thr Ala Gln Ile Met Lys Tyr His Asn Tyr Pro Asn
        195                 200                 205

Lys Gly Leu Lys Asp Tyr Thr Tyr Thr Leu Ser Ser Asn Asn Pro Tyr
    210                 215                 220

Phe Asn His Pro Lys Asn Leu Phe Ala Ala Ile Ser Thr Arg Gln Tyr
225                 230                 235                 240

Asn Trp Asn Asn Ile Leu Pro Thr Tyr Ser Gly Arg Glu Ser Asn Val
                245                 250                 255

Gln Lys Met Ala Ile Ser Glu Leu Met Ala Asp Val Gly Ile Ser Val
            260                 265                 270

Asp Met Asp Tyr Gly Pro Ser Ser Gly Ser Ala Gly Ser Ser Arg Val
        275                 280                 285
```

```
Gln Arg Ala Leu Lys Glu Asn Phe Gly Tyr Asn Gln Ser Val His Gln
    290                 295                 300

Ile Asn Arg Gly Asp Phe Ser Lys Gln Asp Trp Glu Ala Gln Ile Asp
305                 310                 315                 320

Lys Glu Leu Ser Gln Asn Gln Pro Val Tyr Tyr Gln Gly Val Gly Lys
                325                 330                 335

Val Gly Gly His Ala Phe Val Ile Asp Gly Ala Asp Gly Arg Asn Phe
            340                 345                 350

Tyr His Val Asn Trp Gly Trp Gly Val Ser Asp Gly Phe Phe Arg
        355                 360                 365

Leu Asp Ala Leu Asn Pro Ser Ala Leu Gly Thr Gly Gly Ala Gly
    370                 375                 380

Gly Phe Asn Gly Tyr Gln Ser Ala Val Val Gly Ile Lys Pro
385                 390                 395

<210> SEQ ID NO 2
<211> LENGTH: 130
<212> TYPE: PRT
<213> ORGANISM: Artificial Sequence
<220> FEATURE:
<223> OTHER INFORMATION: synthesized polypeptides from Streptococcal
      pyrogenic exotoxic B

<400> SEQUENCE: 2

Gly Ile Ser Val Asp Met Asp Tyr Gly Pro Ser Ser Gly Ser Ala Gly
1               5                   10                  15

Ser Ser Arg Val Gln Arg Ala Leu Lys Glu Asn Phe Gly Tyr Asn Gln
            20                  25                  30

Ser Val His Gln Ile Asn Arg Gly Asp Phe Ser Lys Gln Asp Trp Glu
        35                  40                  45

Ala Gln Ile Asp Lys Glu Leu Ser Gln Asn Gln Pro Val Tyr Tyr Gln
    50                  55                  60

Gly Val Gly Lys Val Gly Gly His Ala Phe Val Ile Asp Gly Ala Asp
65                  70                  75                  80

Gly Arg Asn Phe Tyr His Val Asn Trp Gly Trp Gly Val Ser Asp
                85                  90                  95

Gly Phe Phe Arg Leu Asp Ala Leu Asn Pro Ser Ala Leu Gly Thr Gly
            100                 105                 110

Gly Gly Ala Gly Gly Phe Asn Gly Tyr Gln Ser Ala Val Val Gly Ile
        115                 120                 125

Lys Pro
    130

<210> SEQ ID NO 3
<211> LENGTH: 15
<212> TYPE: PRT
<213> ORGANISM: Artificial Sequence
<220> FEATURE:
<223> OTHER INFORMATION: synthesized polypeptides from Streptococcal
      pyrogenic exotoxic B

<400> SEQUENCE: 3

Ser Val His Gln Ile Asn Arg Gly Asp Phe Ser Lys Gln Asp Trp
1               5                   10                  15

<210> SEQ ID NO 4
<211> LENGTH: 15
<212> TYPE: PRT
<213> ORGANISM: Artificial Sequence
<220> FEATURE:
```

```
<223> OTHER INFORMATION: synthesize polypeptides from Streptococcal
      pyrogenic exotoxic B

<400> SEQUENCE: 4

Glu Ala Gln Ile Asp Lys Glu Leu Ser Gln Asn Gln Pro Val Tyr
1               5                   10                  15

<210> SEQ ID NO 5
<211> LENGTH: 14
<212> TYPE: PRT
<213> ORGANISM: Artificial Sequence
<220> FEATURE:
<223> OTHER INFORMATION: synthesized polypeptide from Streptococcal
      pyrogenic exotoxic B

<400> SEQUENCE: 5

Gln Gly Val Gly Lys Val Gly Gly His Ala Phe Val Ile Asp
1               5                   10

<210> SEQ ID NO 6
<211> LENGTH: 15
<212> TYPE: PRT
<213> ORGANISM: Artificial Sequence
<220> FEATURE:
<223> OTHER INFORMATION: synthesized polypeptides from Streptococcal
      pyrogenic exotoxic B

<400> SEQUENCE: 6

Gly Ala Asp Gly Arg Asn Phe Tyr His Val Asn Trp Gly Trp Gly
1               5                   10                  15

<210> SEQ ID NO 7
<211> LENGTH: 20
<212> TYPE: PRT
<213> ORGANISM: Artificial Sequence
<220> FEATURE:
<223> OTHER INFORMATION: synthesized polypeptides from Streptococcal
      pyrogenic exotoxic B

<400> SEQUENCE: 7

Asn Trp Gly Trp Gly Gly Val Ser Asp Gly Phe Phe Arg Leu Asp Ala
1               5                   10                  15

Leu Asn Pro Ser
            20

<210> SEQ ID NO 8
<211> LENGTH: 23
<212> TYPE: PRT
<213> ORGANISM: Artificial Sequence
<220> FEATURE:
<223> OTHER INFORMATION: synthesized polypeptides from Streptococcal
      pyrogenic exotoxic B

<400> SEQUENCE: 8

Ala Leu Gly Thr Gly Gly Gly Ala Gly Gly Phe Asn Gly Tyr Gln Ser
1               5                   10                  15

Ala Val Val Gly Ile Lys Pro
            20

<210> SEQ ID NO 9
<211> LENGTH: 53
<212> TYPE: PRT
<213> ORGANISM: Artificial Sequence
<220> FEATURE:
<223> OTHER INFORMATION: synthesized polypeptides from Streptococcal
      pyrogenic exotoxic B

<400> SEQUENCE: 9
```

-continued

```
Gly Ala Asp Gly Arg Asn Phe Tyr His Val Asn Trp Gly Trp Gly Gly
1               5                   10                  15

Val Ser Asp Gly Phe Phe Arg Leu Asp Ala Leu Asn Pro Ser Ala Leu
            20                  25                  30

Gly Thr Gly Gly Gly Ala Gly Gly Phe Asn Gly Tyr Gln Ser Ala Val
        35                  40                  45

Val Gly Ile Lys Pro
    50
```